United States Patent [19]

Nagai

[11] Patent Number: 5,058,011
[45] Date of Patent: Oct. 15, 1991

[54] RADIANT RAY CT WITH VIEW DATA INTERPOLATION

[75] Inventor: Hideo Nagai, Tokyo, Japan

[73] Assignee: Yokogawa Medical Systems, Limited, Tokyo, Japan

[21] Appl. No.: 335,665

[22] PCT Filed: Sep. 30, 1987

[86] PCT No.: PCT/JP87/00712
§ 371 Date: Mar. 27, 1989
§ 102(e) Date: Mar. 27, 1989

[87] PCT Pub. No.: WO88/02239
PCT Pub. Date: Apr. 7, 1988

[30] Foreign Application Priority Data

Sep. 30, 1986 [JP] Japan ................... 61-232645
Oct. 27, 1986 [JP] Japan ................... 61-255340

[51] Int. Cl.$^5$ ............... A61B 6/03; G01N 23/04; G06F 15/42
[52] U.S. Cl. ............................. 364/413.18
[58] Field of Search ....................... 364/413.18

[56] References Cited

U.S. PATENT DOCUMENTS 4,680,709  7/1987  Srinivasan et al. ......... 364/413.21
4,682,289  7/1987  Nishihara ................. 364/413.18
4,752,879  6/1988  Brunnett ................. 364/413.21

OTHER PUBLICATIONS

English Language Translation of JP 53-114376 Published Oct. 5, 1978.
English Language Translation of JP 59-183737 Published Oct. 18, 1984.
English Language Translation of JP 58-183146, Published Oct. 23, 1983.

*Primary Examiner*—Clark A. Jablon
*Attorney, Agent, or Firm*—Moonray Kojima

[57] ABSTRACT

A radiant ray CT for reconstructing an image at a high effective rate, high resolution, and high picture quality with a shortened scan time and thus with less exposure. The apparatus comprises a source of radiant ray, such as an X-ray, and a group of detectors disposed in confronting relation with a reconstructive region for accommodating a body to be examined interposed therebetween, wherein scanning is performed according to spatial and timing controls of the radiant ray generating positions so that each of the radiant ray transmitting paths is interpolated with one another substantially at the center of the reconstructive region between adjacent or neighboring view data groups and between confronting view data groups each corresponding to each of the adjacent or neighboring view groups.

18 Claims, 10 Drawing Sheets

RADIANT RAY CT WITH VIEW DATA INTERPOLATION

TECHNICAL FIELD

The present invention relates to a radiant ray CT or a computed tomographing apparatus using a radiant ray, such as X-ray, and more particularly to a radiant ray Ct of the fourth generation having an X-ray source rotatable at an angle of 360°, which provides a reconstructive image of high resolution and high picture quality.

BACKGROUND ART

In a stationary type radiant ray CT (description will be made with respect to the case using an X-ray) called as the fourth generation type in which detectors are disposed along the entire circumference of a circle, an X-ray source is rotated about a reconstructive region for accommodating a body to be examined and the detectors are stationary. A gantry portion of such an apparatus is shown in FIG. 8. In the figure, reference numeral 1 denotes an image reconstructive region for reconstructing a cross-sectional image of the body to be examined disposed interiorly of the gantry portion, and 2 detectors for detecting the X-ray radiated toward the reconstructive region 1. An X-ray source 3 continuously rotates along a circle circumferntially of the reconstructive region 1 while generating a fan-shaped X-ray beam directed toward the reconstructive region 1. The X-ray beam is generated in pulsating manner when the X-ray source 3 is of a pulse type. When the X-ray source 3 is rotating for scanning, data from the respective detectors 2 are sampled at every predetermined angle in synchronization with the generation of the X-ray beam. This type is advantageous in that reliability in terms of mechanism is high because tomographing can be accomplished merely by rotating the X-ray source, a tomographing can be made at a high speed, and reduction of false image, such as a ring artifact, can effectively be achieved because each of the detectors 2 can equally pickup the imaging data in the reconstructive region 1.

In FIG. 9, there is shown a spatial relation between a scan and a data pickup portion in an X-ray CT apparatus. In this figure, the same portions as those shown in FIG. 8 are denoted by the same reference numerals or character. In FIG. 9, character O denotes the center of the reconstructive region 1, LA the circumference of a circle along which the detectors 2 are arranged. Each of the detectors 2 is arranged at an equi-interval and equi-angular-interval. The X-ray source 3 rotates along the circumference of the circle LB, and in the case of the pulse type X-ray source 3, the X-ray is emitted at the points of Xi (i= −n . . . 0 . . . n) or Yi (i= −n . . . 0 . . . n) on the circumference of the circle LB and transmissive data (view data) of the body under examination are collected by the detectors disposed in the positions receiving the fan-shaped X-ray. The data to be collected are limited to those in the range of an angle covering at least the reconstructive region 1.

In order to improve the resolution (spatial resolution) of the reconstructive image, particularly to improve the resolution in the radius direction, a so-called offset detection method has been employed. In this method, assuming that the X-ray beam is generated at the point X0, a straight line connecting the center of the detector D0 and the point X0 is intentionally displaced relative to a straight line connecting the point X0 and the center P of the reconstructive region, in other words, a geometrically identified position in such a relation is detected, whereupon the X-ray beam is generated. The data thus collected and the data collected in the point Y0 are in such a relation that the transmissive X-ray paths are not in coincidence with each other at the position in the vicinity of the center O of the reconstructive region 1. With such a method, it is contemplated to increase effective sampling data upon interpolation.

It is, however, extremely difficult to improve the resolution more than a limited amount. Although there are various methods, such as a method of performing the scanning with respect to a greater number of detectors arranged in higher density, or a method of performing a multi-rotational scanning while changing an amount of offset every rotation by the use of detectors having a narrow-width opening, the scan time is inadversely prolonged, the amount of exposure markedly increases, and an expensive apparatus is required.

DISCLOSURE OF THE INVENTION

An object of this invention is to provide a radiant ray CT in which scan time is shortened and thus an effective sample rate is high with a lesser amount of exposure and an image reconstruction of high resolution and high picture quality is obtained.

In order to solve the aforementioned problems, there is provided a radiant ray CT in which a source of radiant ray, such as an X-ray, and a group of detectors are disposed in confronting relation with interposing a reconstructive region for accommodating a body to be examined therebetween, characterized in that scanning is performed according to spatial and timing controls of the radiant ray generating positions so that each of the radiant ray transmitting paths is interpolated with one another at least at the center of the reconstructive region between adjacent or neighboring view data groups and between confronting view data groups. The radiant ray transmitting path is intended to mean a center-passing straight line in terms of geometric optics in the case where the radiant ray is expanded in shape.

By emitting the radiant ray upon controlling a spatial position of the radiant ray generation, the radiant ray transmitting paths of a view data in an arbitrary position and its neighboring view data, and the view data in the confronting position and its neighboring view data are not overlapped with each other in the vicinity of the center of the reconstructive region and are interpolated with one another, thus those data are obtained as different data.

BEST MODE FOR CARRYING OUT THE INVENTION

Figure 1:
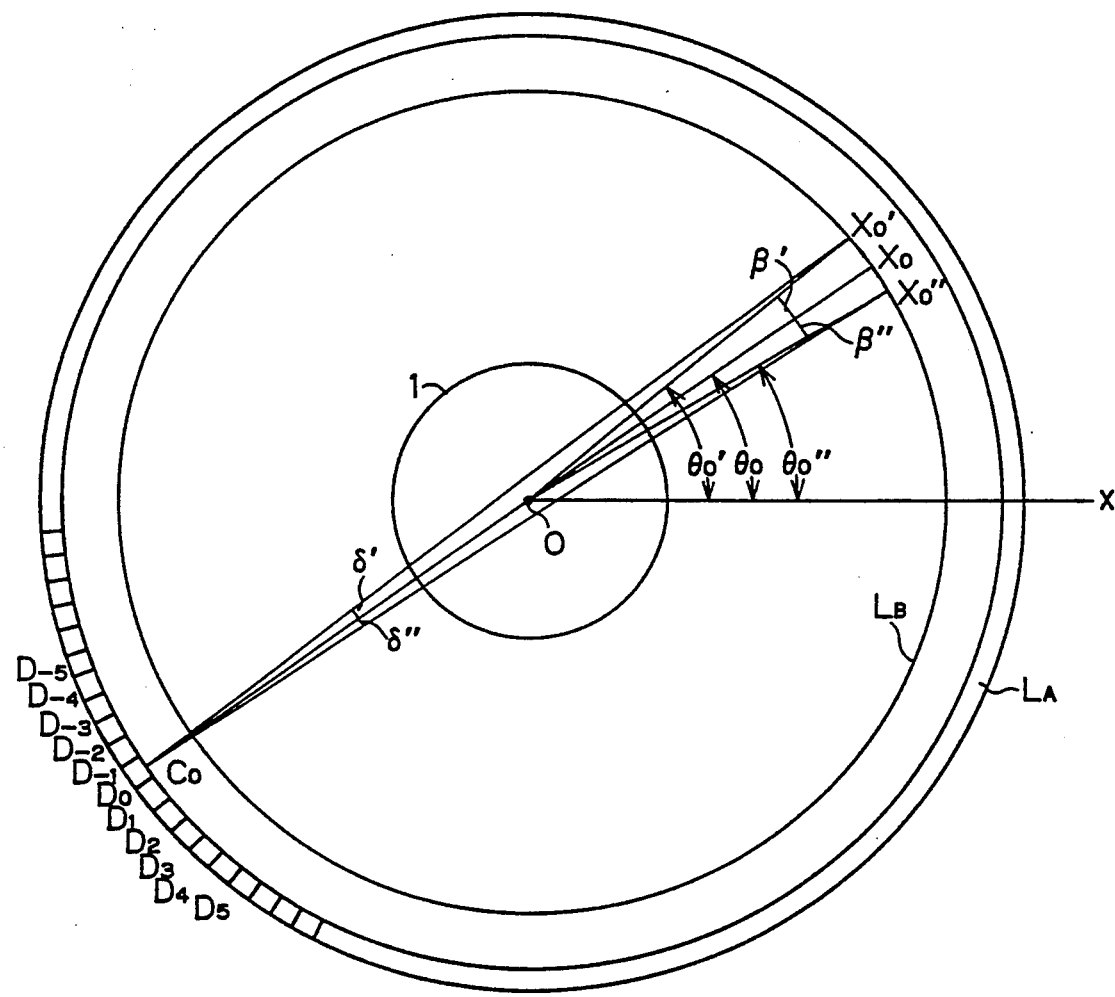
FIG. 1 is an explanatory diagram illustrating a principle of the present invention.
Figure 8:
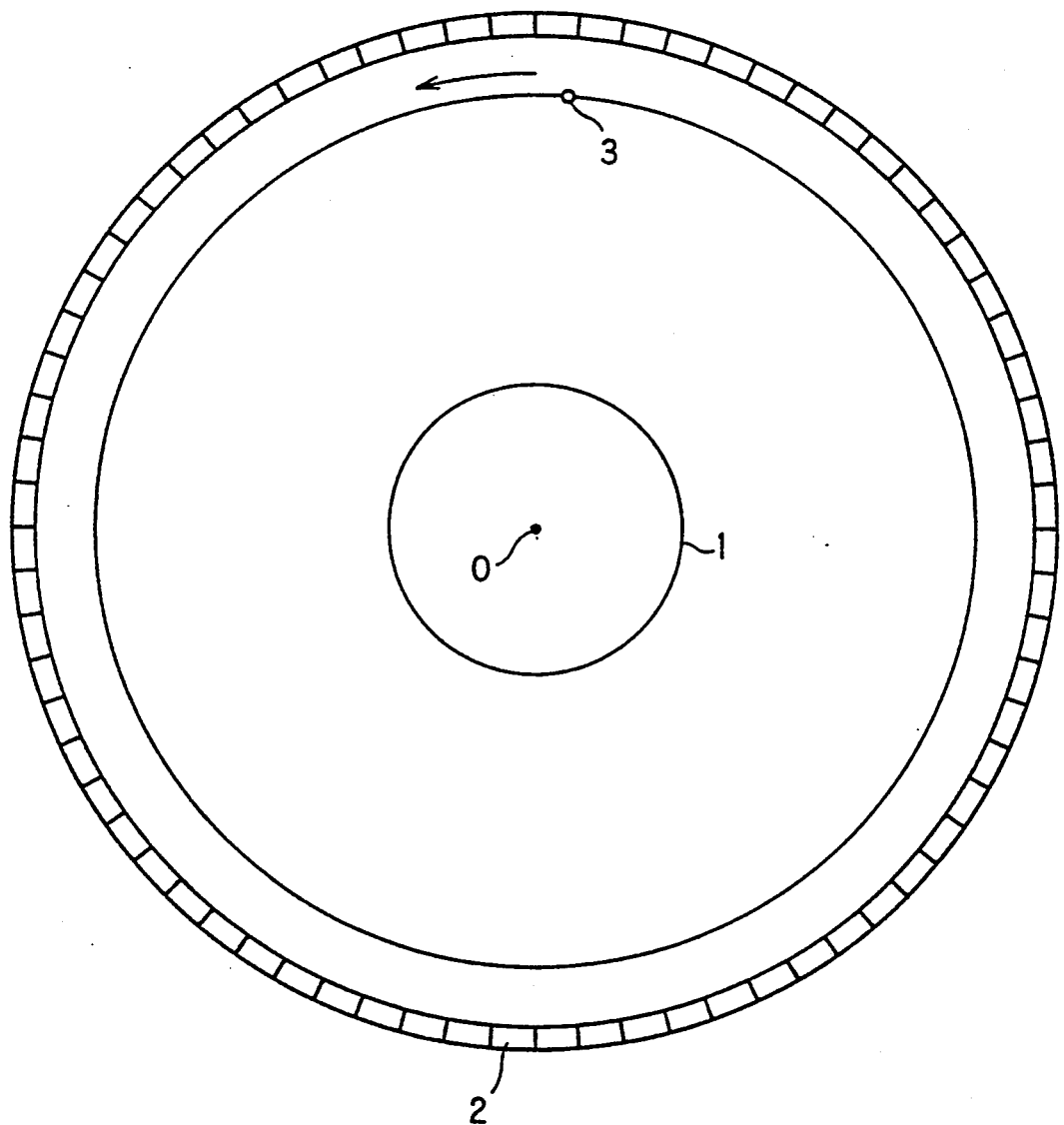
FIG. 8 is a diagram showing a gantry portion.
Figure 9:
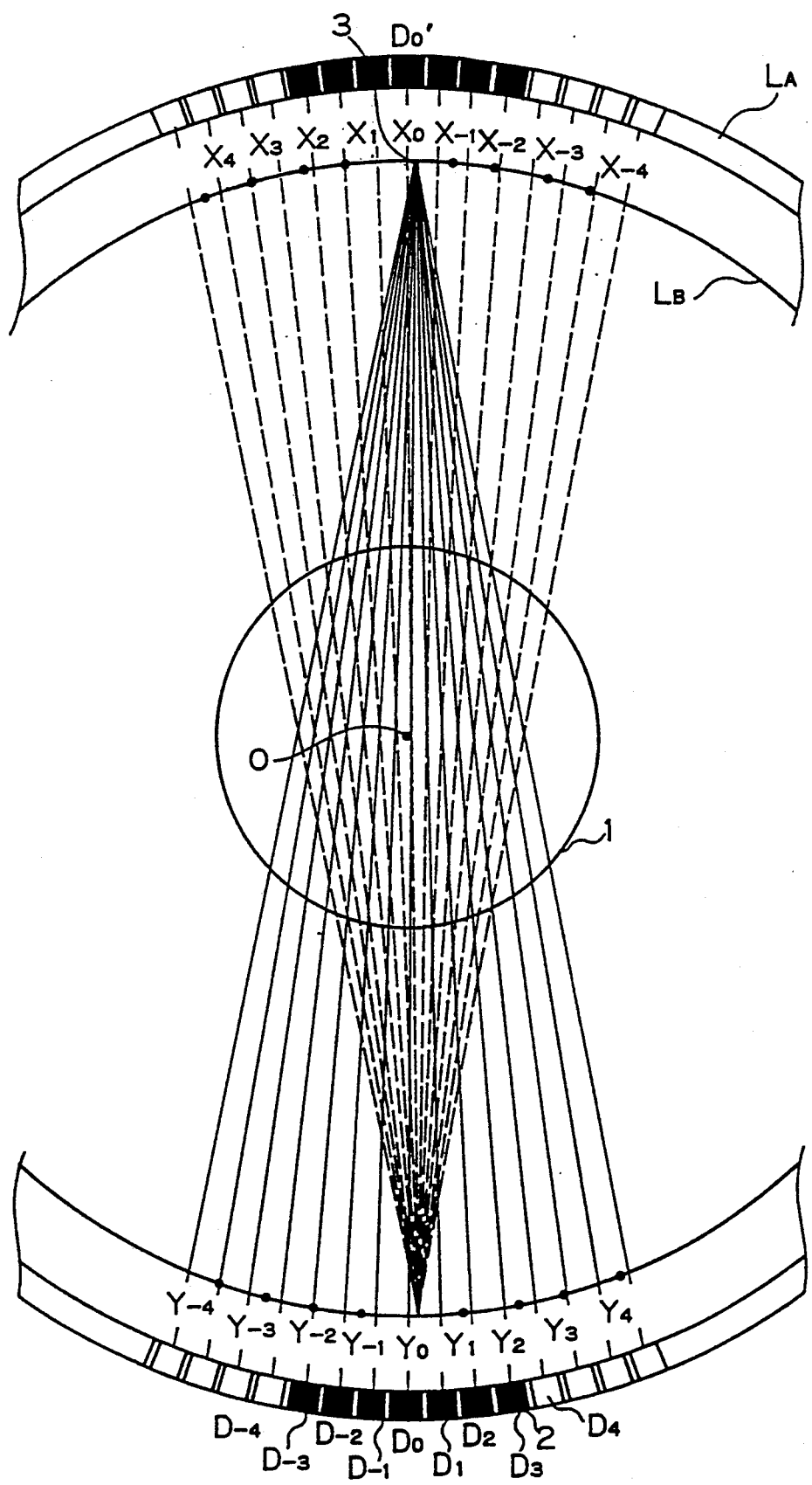
FIG. 9 is a diagram showing a spatial arrangement of the portions receiving scan data according to an ordinary offset detection method.

Hereinafter, the present invention will be described in detail with reference to the accompanying drawings. First of all, the principle of the present invention will be described. FIG. 1 is an explanatory diagram for description of the principle of the present invention, in which illustrated is a geometrical arrangement of a scanning system. In FIG. 1, the same reference numerals and characters as used in FIGS. 8 and 9 denote the same parts as those shown therein. Detectors Di (i = −n ... 0 ... n) are fixedly arranged along the circumference of a circle LA at an equi-interval and an equi-angular-interval, in which a detector D0 is disposed at the center with respect to the remainder. An X-ray generating source 3 moves along the circumference of a circle LB, and emits a fan-shaped X-ray at the respective points on LB in the case where the X-ray generating source 3 is of a pulse type. With respect to the intersection of the circumference of the circle LB and the straight line connecting O and the center C0 of the detector D0, the point at the opposite side of D0 with respect to O is defined as X0 and an angle formed between OX0 and the positive direction of an X-axis is defined as $\theta 0$. Intersections of the circumference of the circle LB and straight lines forming angles $\delta'$ and $-\delta''$ as viewed from the point C0 with respect to a segment of line C0X0 are defined as X0' and X0'', respectively. The angles formed between the segment OX0' and the positive direction of the X-axis and between the segment OX0'' and the positive direction thereof are defined respectively as $\theta 0'$ and $\theta 0''$, and the angles formed between the segments OX0' and C0X0 and between the segments OX0'' and C0X0 are defined respectively as $\beta'$ and $\beta''$.

Under the movement of the X-ray source 3 along the circumference of the circle LB, the X-ray beam is emitted from the X-ray source 3 toward the reconstructive region 1 and the transmissive radiation is incident to the detector Di. On condition that the X-ray beam is emitted from an arbitrary position (for example, X0'), its a neighbouring position (for example, X0''), a position being rotated by 180° from the above-mentioned arbitrary position and the neighboring position of the latter, the respective positions where the X-ray source 3 emits the X-ray beam are obtained so that the X-ray transmission paths by the respective irradiations are interpolated with one another at the position in the vicinity of the center O.

It is assumed now that the following scanning is performed, in which the number of positions that the X-ray source 3 emits the X-ray beam is 2N and the X-ray source 3 moves in counterclockwise direction.

Figure 2:
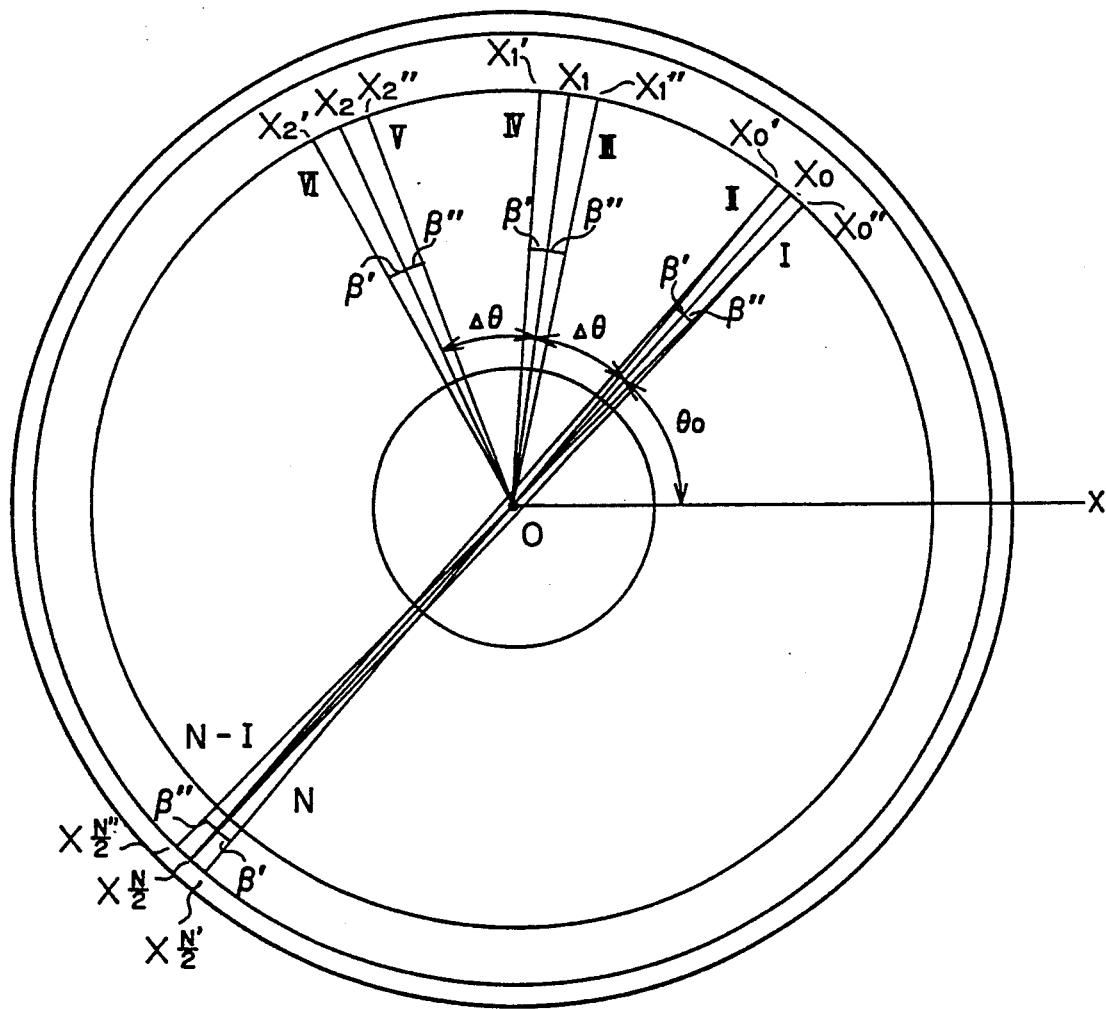
FIG. 2 is a diagram showing irradiating positions according to the present invention.

The view positions by the X-ray source 3 are assumed to be as those shown in FIG. 2.

| | |
|---|---|
| The first view is | $\theta 0 - \beta''$ |
| The second view is | $\theta 0 + \beta'$ |
| The third view is | $\theta 0 + \Delta\theta - \beta''$ |
| The fourth view is | $\theta 0 + \Delta\theta + \beta'$ |
| The (N + 1)-th view is | $\theta 0 + 180° - \beta''$ (the view opposing to the first view) |
| The (N + 2)-th view is | $\theta 0 + 180° + \beta'$ |
| The (2N − 1)-th view is | $\theta 0 + 360° - \Delta\theta - \beta''$ |
| The 2N-th view is | $\theta 0 + 360° - \Delta\theta + \beta''$ |

Those view positions correspond to the scannings carried out at positions X0'', X0', X1'', X1', X2'', X2' and so on.

Figure 3:
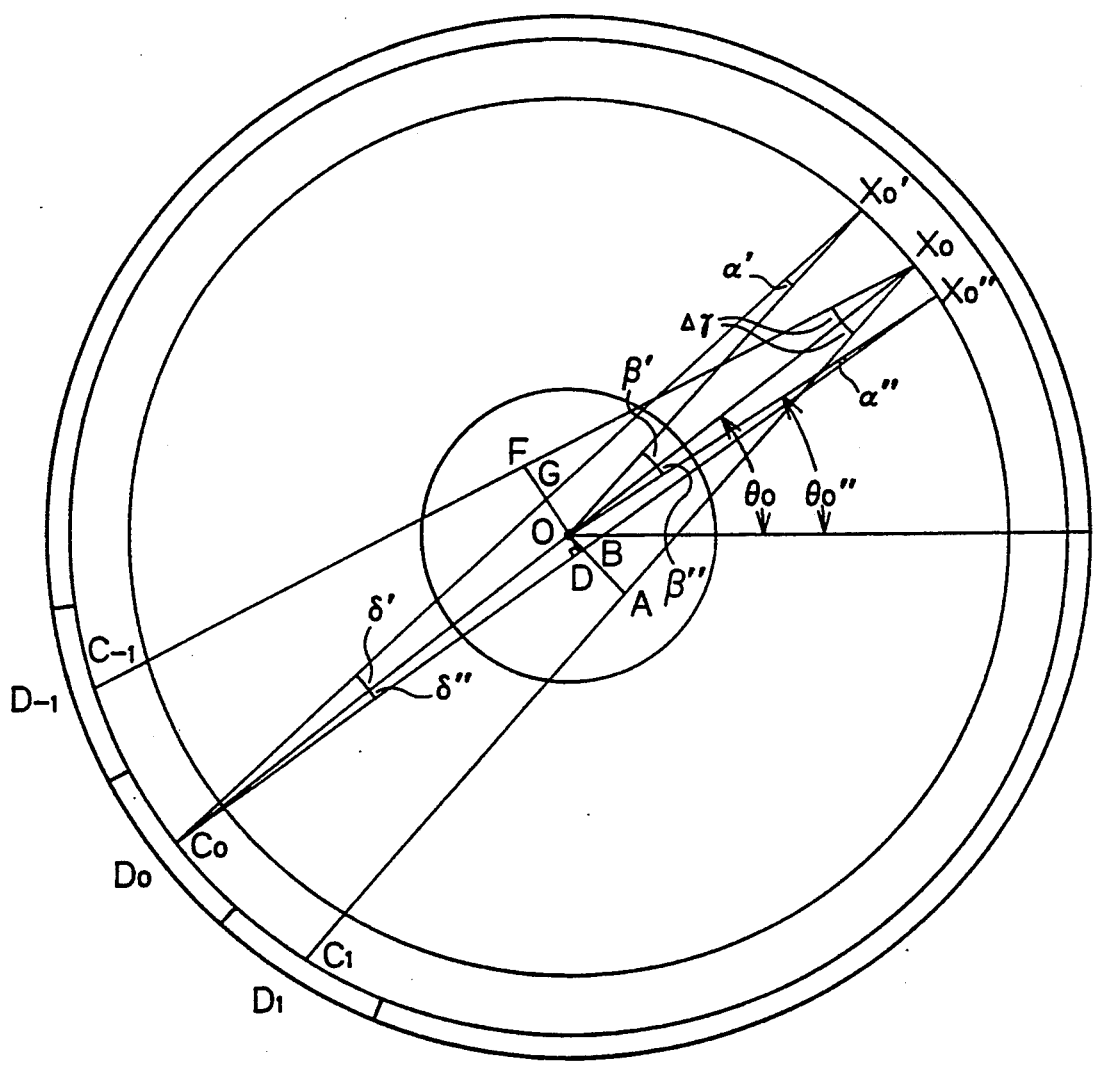
FIG. 3 is an explanatory diagram for description of calculations of $\beta'$ and $\beta''$.

The settings of $\beta'$ and $\beta''$ will be described while referring to FIG. 3. In order to facilitate the description, the detectors and the generating points of the X-ray beam are depicted at enlarged scale. In FIG. 3, the same characters as those in FIG. 1 define the same amounts or quantities. Denoted by characters D-1, D0 and D1 are neighboring detectors and C-1, C0 and C1 are the centers thereof, respectively. The angle formed between the segments C0X0 and C1X0 is defined as $\Delta\gamma$, the angle formed between the segments C0X0 and C0X0'' as $\delta''$, and the angle formed between the segments OX0'' and C0X0'' as $\alpha''$. The lengths of the segment C0X0 and OX0 are defined as L and l, respectively. A point A is plotted on the segment C1X0 so that the length from X) TO A is equal to the segment OX0, and the intersection of the segments $\overline{C0X0''}$ and $\overline{OA}$ is defined as point B.

Since in the triangle C0OX0'', $\beta''$ is an exterior angle, $$\beta'' = \delta'' + \alpha'' \tag{1}$$

Since $\Delta\gamma$, $\delta''$ are extremely small, the following equation is established:

$$\overline{OA} \approx \overline{OX0} \cdot \angle OX0c1 = l \cdot \Delta\gamma \tag{2}$$

Selecting so that $\overline{OB} = (\frac{1}{8})\overline{OA}$, in the triangle OC0B, $$\overline{OB} = \overline{C00} \cdot \angle OC0B = (L - l)\delta'' \tag{3}$$
$$(L - l)\delta'' \approx OB = (1/8)OA$$

From equations (2) and (3), $$\delta'' \approx l \cdot \Delta\gamma / \{8(L - l)\} \tag{4}$$

Assuming that the perpendicular line drawn from O to the baseline $\overline{C0X0''}$ is $\overline{OD}$ and the length thereof is h, $$\text{Since } \overline{OX0'} = \overline{OX0} = l \tag{5}$$
$$\sin \alpha'' = h/l$$
$$\sin \delta'' = \overline{OD}/\overline{OCO} = h/(L - l)$$
$$\therefore \alpha'' = \sin - 1[\{(L - l)/l\} \cdot \sin \delta'']$$

From equations (1), (4) and (5), $$\beta'' = \sin^{-1}[\{(L - l)/l\} \cdot \sin \delta''] + l \cdot \Delta\gamma / \{8(L - l)\} \tag{6}$$

With respect to $\beta'$, the center C-1 of the detector D-1 adjacent to the detector D0 and X0 is connected, and on the segment C-1X0 a point F is plotted so that the length from X0 to the point f is equal to the length of the segment OX0. The intersection of the segments OF and C0X0' is defined as G.

Selecting so that $\overline{OG} = (\frac{1}{8})\overline{OF}$, the following equations are obtained:

$$\delta' = 3 \cdot l \cdot \Delta\gamma/\{8(L - l)\} \quad (7)$$
$$\alpha' = \sin^{-1}[\{(L - l)/l\} \cdot \sin \delta'] \quad (8)$$
$$\beta' = \sin^{-1}[\{(L - l)/l\} \cdot \sin \delta'] + 3 \cdot \Delta\gamma/\{8(L - l)\} \quad (9)$$

Figure 4:
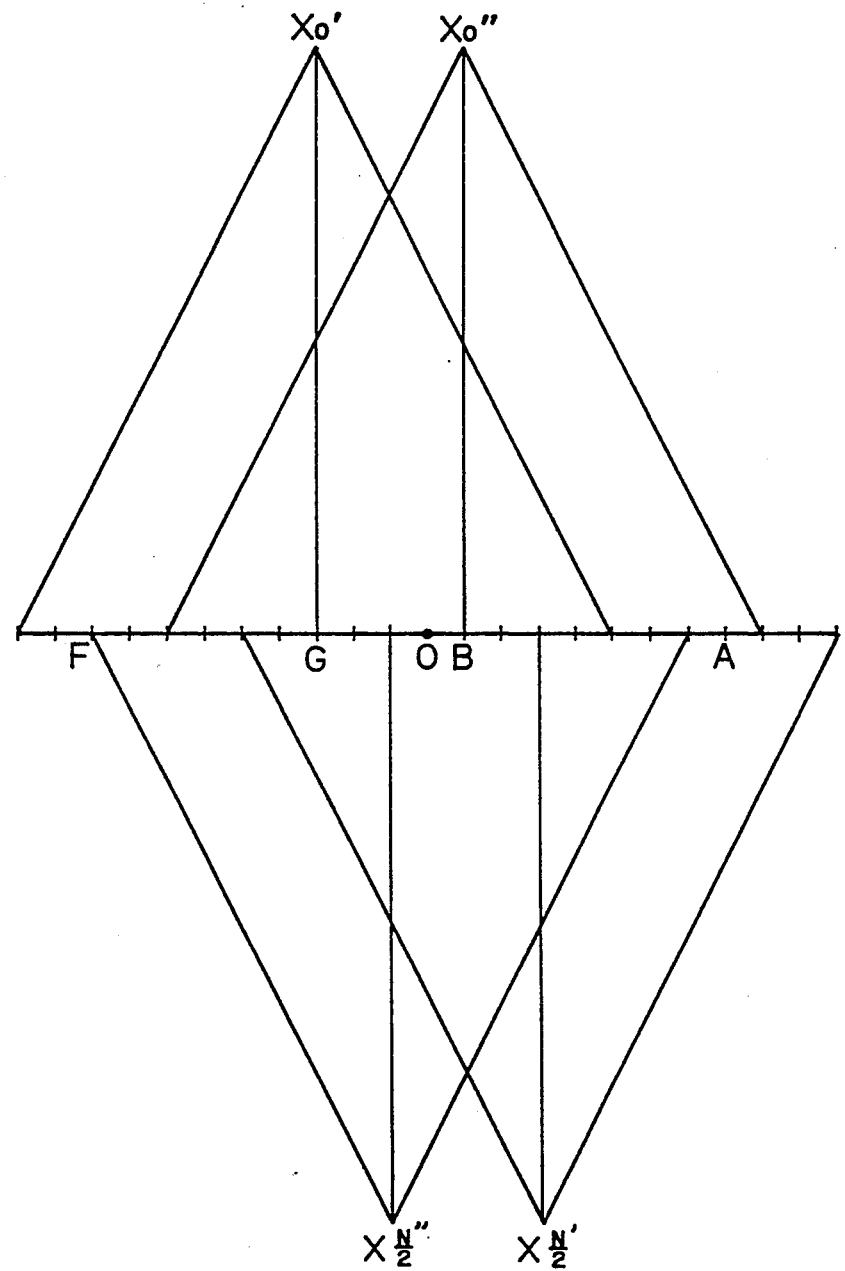
FIG. 4 is an enlarged explanatory diagram for description of interpolation.

Selecting $\beta'$ and $\beta''$ as described above, in the vicinity of the center of the reconstructive region, the transmission paths of the center of the X-ray beam from X0" and X0' are displaced from the center O by $-\frac{1}{8}$ and $\frac{3}{8}$, respectively, and the transmission paths thereof from Xn/2" and XN/2' are displaced by $\frac{1}{8}$ to $\frac{3}{8}$. Meanwhile, the sign for the offset is defined so that plus (+) is given to that occurring in the left side with respect to the direction from O toward X0 and minus (−) is given to that occurring in the right side with respect thereto. Such relation is illustrated in FIG. 4 in which the same characters as those shown in FIG. 3 are used to indicate the same positions. XN/2' and XN/2" indicate the positions of the X-ray source 3, which positions are in symmetrical relation with respect to the centers of X0' and X0". As is apparent from the figure, the transmission path of the beam center from the first view X0" is displaced by $\frac{1}{8}$ of OA from the center O, and the transmission path of the beam center from X0' is displaced by $\frac{3}{8}$ thereof from the center O in the opposite side. XN/2" is in the position rotated by 180° from X0", and the transmission path of the beam center from XN/2" is displaced by $\frac{1}{8}$ from the center O in the opposite side. XN/2' is in the position rotated by 180° from X0', and the transmission path of the beam center from XN/2' is displaced by $\frac{3}{8}$ from the center O in the opposite side of X0'. Consequently, two adjacent views and another two adjacent view each being confronted to each of the former two views are in a 2/8 interval interpolating relation.

Figure 5:
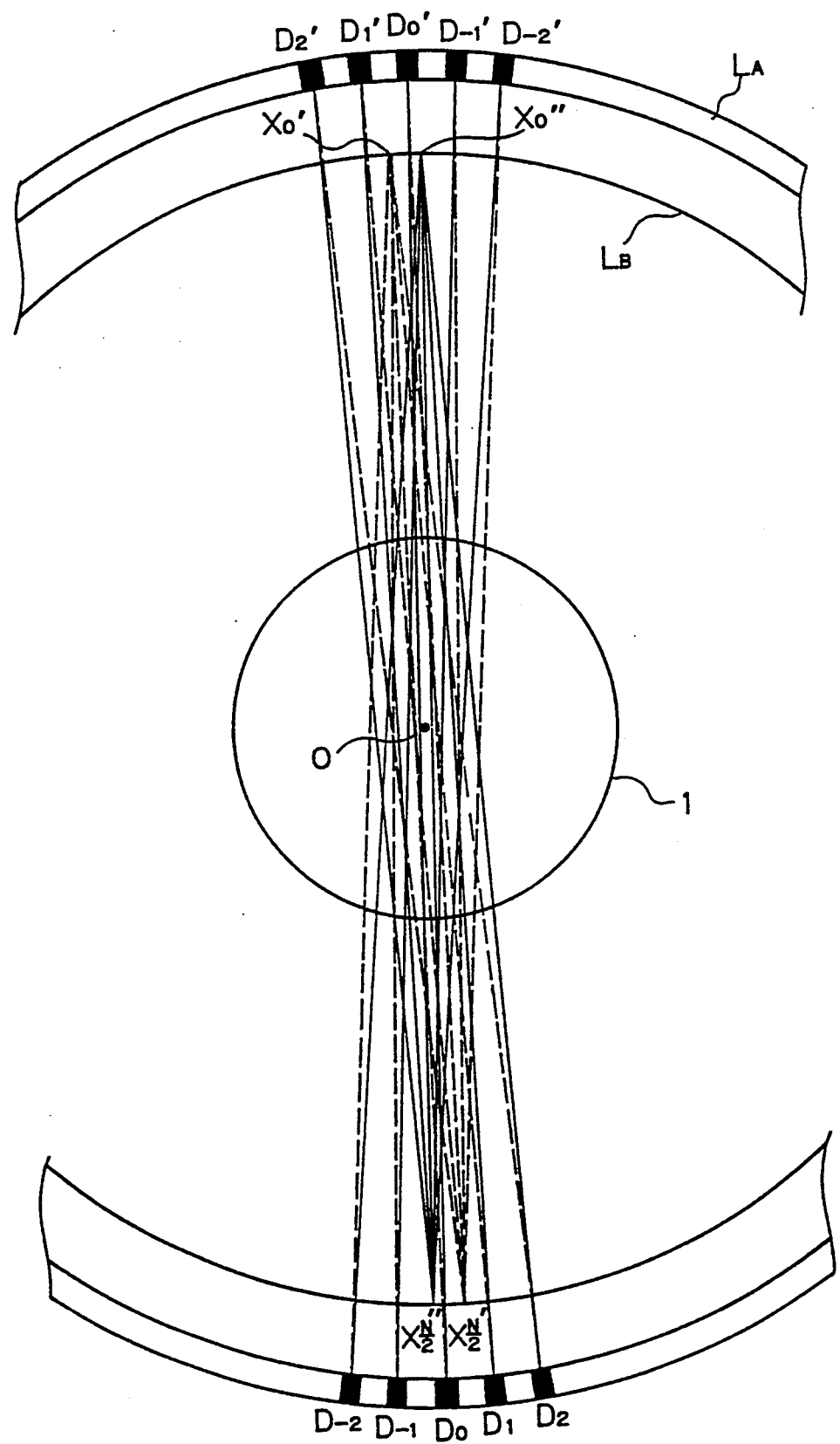
FIG. 5 is a diagram showing an irradiation by an X-ray source equipped in the apparatus.

FIG. 5 is a diagram for description of the interpolation. In the vicinity of the center O, the transmission paths of the X-ray beams from X0', X0", XN/2' and XN/2" are interpolated with one another.

Although in the foregoing description, description has been made with respect to the positions X0, X0' and X0" and their symmetrical positions, the same effects can of course be obtained even if the X-ray source 3 is at any positions on the circumference of the circle LB.

Figure 6:
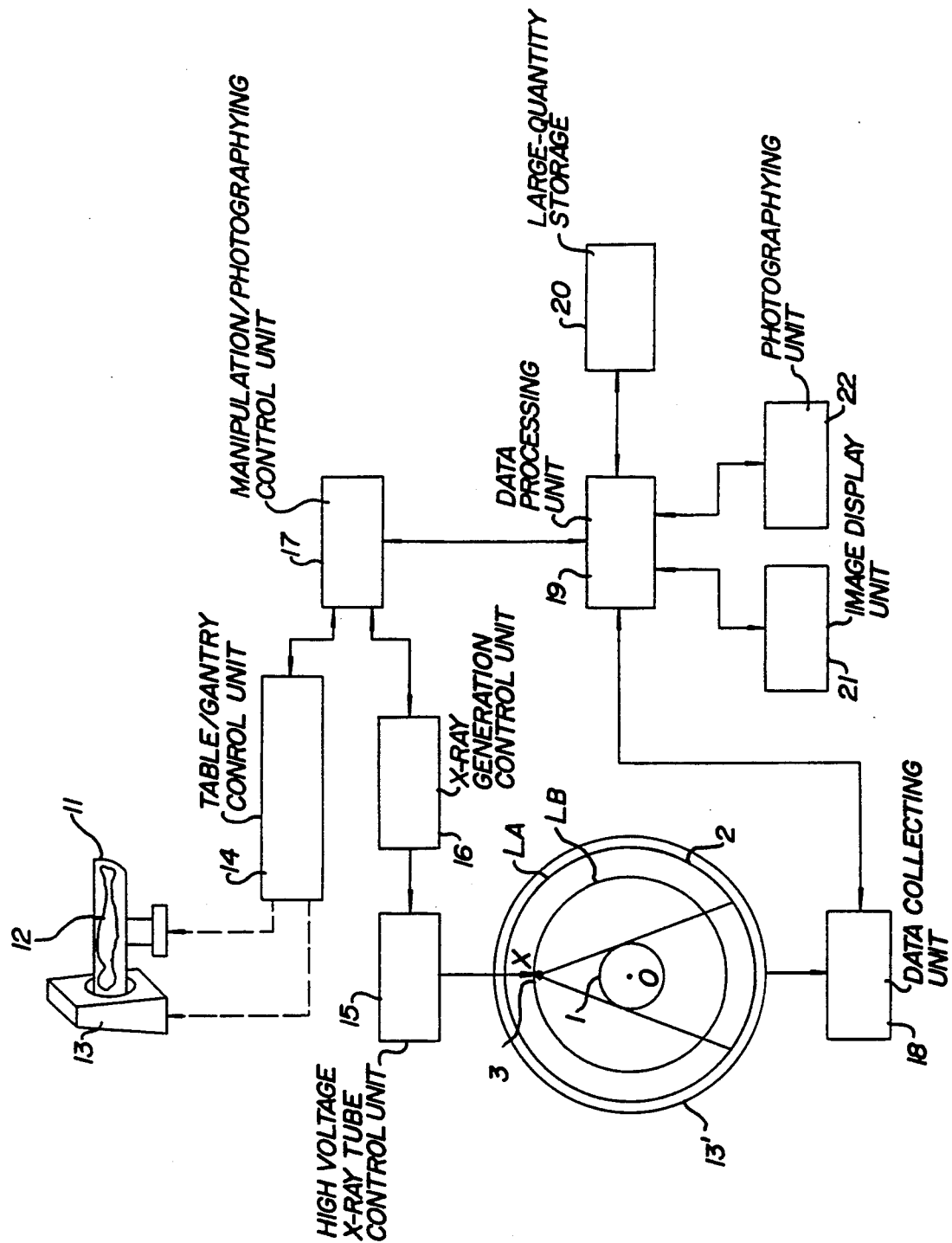
FIG. 6 is a diagram showing a CT apparatus according to one embodiment of the present invention.

One embodiment of the X-ray CT using the above-described principle is shown in FIG. 6. In the figure, reference numeral 11 denotes a table for placing the body 12 to be examined. The table 11 is horizontally moved so that the body 12 is entered into the hole formed in the center portion of a gantry 13. The gantry 13 has its cross-section as shown by numeral 13'. The X-ray tube X of an X-ray source 3 rotates about the center O of a reconstructive region 1 and moves along the circumference of a circle LB. Detectors 2 are fixedly arranged on its outer circumference of a circle LA. A table/gentry control unit 14 controls the table 11 so that the body 12 is appropriately disposed within the reconstructive region, and further controls the rotations of the X-ray tube X. A high voltage X-ray tube control unit 15 supplies a high voltage to the X-ray tube X and is controlled by an X-ray generation control unit 16. A manipulation/photographing control unit 17 controls the manipulation and photographic timings of both the table/gentry control unit 14 and the X-ray generation control unit 16.

A data collecting unit 18 collects data indicative of magnitudes of the transmitted X-ray beams which are detected in the detectors 2, and the data thus collected are fed to a data processing unit 19. A large-quantity storage 20 stores the data fed from the data processing unit 19. An image display unit 21 displays an image reconstructed by the data processing unit 19 and a photographing unit 22 takes a picture of the image thus obtained.

Description will next be made with respect to an operation of the apparatus as arranged as above. In response to the control signal fed from the manipulation/photographing control unit 17, the table/gentry control unit 14 causes the table 11 on which the body 12 is placed to feed into the gantry 13 and further causes the X-ray source 3 to rotate and simultaneously controls the X-ray generation control unit 16. The X-ray generation control unit 16 applies a high voltage to the X-ray tube 3, as described in conjunction with the principle explanatory diagram, while controlling the radiation timings of the X-ray tube 3 in response to the signal fed to the high-voltage X-ray control unit 15. The detectors 2 detects the magnitude of the X-ray beam which has transmitted through the reconstructive region 1 and the resultant data is collected by the data collecting unit 18. The data thus collected are subjected to processings, such as logarithmic transform, collection of the X-ray magnitude, in the data processing unit 19 and the resultant data is stored in the large-quantity storage 20. In this manner, when the data for the 2N views are collected, those are subjected to usual large reconstruction processing in the data processing unit 19, the resultant image is displayed on the image display unit 21 and is photographed by the photographing unit 22 when needed.

As described above, since the view data resulting from the X-ray irradiated from the adjacent positions and from their confronting positions are completely interpolated in the vicinity of the center of the reconstructive region 1, the following advantages are obtained:

(1) A CT apparatus can be provided which is of a short scan time and thus of a high-speed scan with low exposure amount in comparison with a conventional high resolution CT.

(2) A higher resolution and higher picture quality CT apparatus can be provided with the same degree of rotational angle and exposure amount as those in the conventional CT.

(3) Extremely high spatial resolution can be obtained with the same photographing system (X-ray generation source with a focusing size inclusive, number of detectors, and geometrical arrangement) if the width of the opening of the detector is sufficiently narrowed.

(4) By defining a view group containing a plurality of views, more than three, which are in neighboring relation with one another and another view group in confronting relation to the former view group as described above, a CT can be provided which is higher in resolution and less in artifact.

It should be noted that the present invention is not limited to the above-described embodiment, but the following scan be may carried out.

Figure 7:
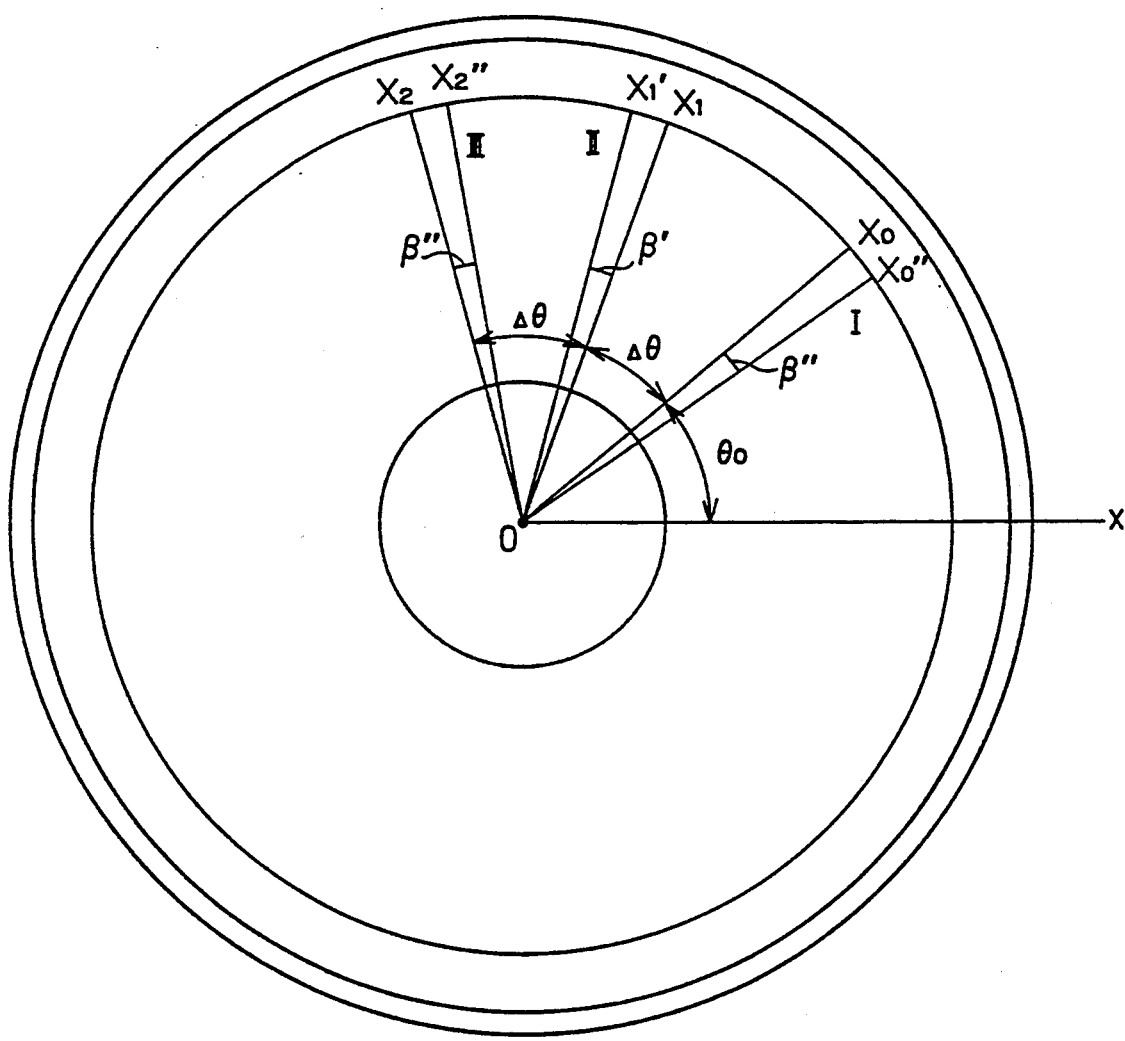
FIG. 7 is a diagram showing irradiating positions according to another embodiment of the present invention.

For example, the scan may be carried out according to the method shown in FIG. 7 (view number: N), in which:

| The first view is | $\theta 0 - \beta''$ |
| The second view is | $\theta 0 + \Delta\theta + \beta'$ |
| The third view is | $\theta 0 + 2\Delta\theta - \beta''$ |
| The fourth view is | $\theta 0 + 3\Delta\theta + \beta'$ |

-continued

| | |
|---|---|
| The (N/2 + 1)-th view is | $\theta_0 + 180° - \beta''$ |
| The (N/2 + 2)-th view is | $\theta_0 + 180° + \Delta\theta + \beta'$ |
| The (N − 1)-th view is | $\theta_0 + 360° - 2\Delta\theta - \beta''$ |
| The N-th view is | $\theta_0 + 360° - \Delta\theta + \beta'$ |

Those view positions correspond to the scannings carried out at positions X0″, X1′, X2″, X3′, ..., XN/2+1″, XN/2+2′, ..., XN−1, Xn′.

The following scanning may be performed, in which:

| | |
|---|---|
| The first view is | $\theta_0 - \beta'$ |
| The second view is | $\theta_0 + \Delta\theta + \beta''$ |
| The third view is | $\theta_0 + 2\Delta\theta + \beta'$ |
| The fourth view is | $\theta_0 + 3\Delta\theta - \beta''$ |

Those view positions corresponds to the scannings carried out at positions X0′, X1″, X2°, X3″ and so on.

It goes without saying that the scanning in the CW direction may of course possible. The $\Delta\theta$ may be given differently for each of the views. In addition, LA may be inside of LB. Specifically, for high resolution, the detectors may be arranged inside the X-ray source 3 (which is an arrangement in which the detectors are retracted to avoid the transmission of the X-ray beam). The values for $\beta'$ and $\beta''$ in both equations (9) and (6) may be replaced by another values. In this case, $\delta''$ and $\delta'$ in equation (6) are replaced by $\delta'$ and $\delta''$ in equation (9), respectively. A variety of modifications may be made with respect to the arrangement of the X-ray CT other than that illustrated as the embodiment. Moreover, various image reconstructive algorithms may be employed.

Selecting $\beta'$ and $\beta''$, $\delta'$ and $\delta''$, and $\alpha'$ and $\alpha''$ to $\beta$, $\delta$ and $\alpha$, respectively, as given by the following equations, $$\beta = \delta + \alpha$$
$$\delta = 1 \cdot \Delta\gamma/4(L - 1)$$
$$\alpha = \sin[\{(L - 1)/1\}\sin\delta]$$

the following scan can be carried out. It should be noted that the scan is carried out in counterclockwise direction.

| | |
|---|---|
| The first view is | $\theta_0 - \beta$ |
| The second view is | $\theta_0 + \beta$ |
| The third view is | $\theta_0 + \Delta\theta - \beta$ |
| The fourth view is | $\theta_0 + \Delta\theta + \beta$ |
| The N-th view is | $\theta_0 + (-1)^N \cdot \beta + [(N - 1)/2] \cdot \Delta\theta$ |

Those view points correspond to the scannings carried out at positions X0″, X0′, X1″, X1′ and so on.

Figure 10:
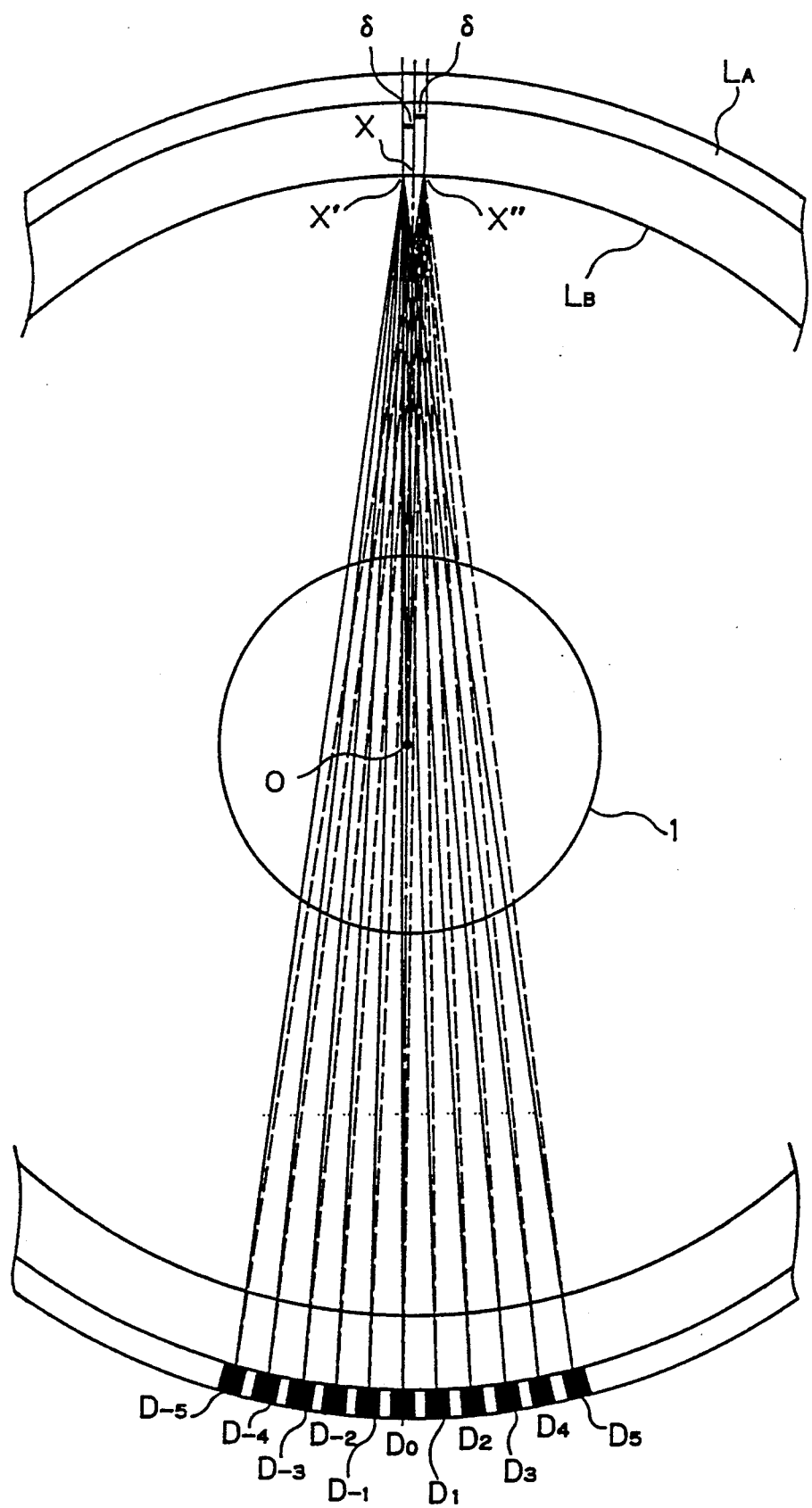
FIG. 10 is a diagram showing irradiating positions according to still another embodiment of the present invention.

The geometrical relation between the (2i−1)-th and the 2i-th view of the scan data is as shown in FIG. 10. In a considerable are of the reconstructive region, the respective X-ray transmission paths are interpolated with one another and effective sample data are increased.

The similar results can be obtained if the scan data are collected in a manner as follows.

| | |
|---|---|
| The first view is | $\theta_0 - \beta$ |
| The second view is | $\theta_0 + \Delta\theta + \beta$ |
| The third view is | $\theta_0 + 2\Delta\theta - \beta$ |
| The N-th view is | $\theta_0 + (-1)^N \cdot \beta + (N - 1) \cdot \Delta\theta$ |

Those view positions correspond to the scannings carried out at positions X0″, X1′, X2″, X3′ and so on.

According to the principle as described above, reconstructive images of high resolution and high picture quality can be obtained with a small scan region of about 180°+a and thus with a high speed scanning. According to the embodiments, the scan data collecting range is 180°+a (a being a fan angle including the reconstructing region) or more than this, therefore, the following advantages can be obtained.

(1) The scan time can be shortened can thus a higher speed scan can be achieved in comparison with the 360° rotate type.

(2) A high resolution and a high picture quality imaging are ensured with a reduced rotational angle.

(3) Influence of the living body's motion can be reduced and the burden upon patients can be decreased.

(4) An apparatus can be provided which affords a higher resolution with a limited small range rotational angle by mutually performing interpolations with respect to the X-ray transmission paths resulting from more than three adjacent views (or neighboring views).

As described in detail, according to the present invention, a high speed scan can be accomplished and thus the scan time can be reduced, and an apparatus can be provided which affords a high resolution and a high picture quality image with low exposure amount. In addition, the pain and burden upon the patient can be reduced and further influence of the body's motion can be decreased. As such, the present invention is practically available in many aspects.

Although the present invention has been described with respect to a best mode for carrying out the invention, a variety of modifications may be made for a skilled artisan in the field of technology to which the present invention pertains without departing from the scope of the invention defined in the appended claims.

I claim:

1. In a radiant ray CT apparatus comprising a source for generating radiant rays from one or more positions and directed in one or more transmitting paths, and a group of detectors, with a reconstructing region therebetween for accommodating a body to be examined therein; the improvement comprising means for performing a scan of the body according to spacing and timing controls of the radiant ray positions so that each of the one or more transmitting paths resulting from alternate adjacent or alternate neighboring view data group is interpolated with one another at substantially the center of the reconstructing region and without any offset.

2. The apparatus of claim 1, wherein the radiant ray path on a first scan is at a first angle on one side of a first ray position, and the radiant ray path on a second scan is at a second angle on the other side of the first ray position, said first and second angles being defined with said center being at their vertex.

3. The apparatus of claim 2, wherein said first and second angles are equal.

4. The apparatus of claim 2, wherein the first angle is clockwise, and the second angle is counterclockwise and the second ray position is counterclockwise.

5. The apparatus of claim 1, wherein the radiant ray path on a first scan is at a first angle on a clockwise or counterclockwise side of a first ray position, and the radiant ray path on a second scan is at a second angle on the opposite side of a second ray position, said first and second angles being defined with said center being at their vertex.

6. The apparatus of claim 5, wherein said first and second angles are equal.

7. The apparatus of claim 5, wherein the radiant ray path on a third scan is at a third angle on either side of a third ray position, said third angle being defined with said center being at its vertex.

8. The apparatus of claim 7, wherein said third angle is equal to the first and second angles, and wherein said third ray position is counterclockwise and said third angle is clockwise.

9. The apparatus of claim 7, wherein said third angle is counterclockwise.

10. In a radiant ray CT apparatus comprising a source for generating radiant rays from one or more positions and directed in one or more transmitting paths, and a group of detectors, with a reconstructing region therebetween for accommodating a body to be examined therein; the improvement comprising means for performing a scan of the body acccording to spacing and timing controls of the radiant ray positions so that each of the one or more transmitting paths is interpolated with one another at substantially the center of the reconstructing region without any offset between alternate adjacent view data groups or alternate neighboring view data groups and between confronting view data groups each corresponding to the alternate adjacent view data groups or alternate neighboring view data groups.

11. The apparatus of claim 10, wherein the radiant ray path on a first scan is at a first angle on one side of a first ray position, and the radiant ray path on a second scan is at a second angle on the other side of the first ray position, said first and second angles being defined with said center being at their vertex.

12. The apparatus of claim 11, wherein said first and second angles are equal.

13. The apparatus of claim 10, wherein the radiant ray path on a first scan is at a first angle on a clockwise or counterclockwise side of a first ray position, and the radiant ray path on a second scan is at second angle on the opposite side of a second ray position, said first and second angles being defined with said center being at their vertex.

14. The apparatus of claim 13, wherein said first and second angles are equal.

15. The apparatus of claim 14, wherein the first angle is clockwise, and the second angle is counterclockwise and the second ray position is counterclockwise.

16. The apparatus of claim 13, wherein the radiant ray path on a third scan is at a third angle on either side of a third ray position, said third angle being defined with said center being at its vertex.

17. The apparatus of claim 16, wherein said third angle is equal to the first and second angles, and wherein said third ray position is counterclockwise and said third angle is clockwise.

18. The apparatus of claim 16, wherein said third angle is counterclockwise.

* * * * *